United States Patent
Ifantides

(10) Patent No.: US 11,738,022 B2
(45) Date of Patent: Aug. 29, 2023

(54) METHODS FOR INDUCING PUPIL DILATION

(71) Applicant: THE REGENTS OF THE UNIVERSITY OF COLORADO, A BODY CORPORATE, Denver, CO (US)

(72) Inventor: Cristos Ifantides, Denver, CO (US)

(73) Assignee: The University of Colorado, a body corporate, Denver, CO (US)

( * ) Notice: Subject to any disclaimer, the term of this patent is extended or adjusted under 35 U.S.C. 154(b) by 140 days.

(21) Appl. No.: 16/763,177

(22) PCT Filed: Nov. 6, 2018

(86) PCT No.: PCT/US2018/059469
§ 371 (c)(1),
(2) Date: May 11, 2020

(87) PCT Pub. No.: WO2019/094390
PCT Pub. Date: May 16, 2019

(65) Prior Publication Data
US 2020/0383978 A1    Dec. 10, 2020

Related U.S. Application Data

(60) Provisional application No. 62/584,200, filed on Nov. 10, 2017.

(51) Int. Cl.
| | | |
|---|---|---|
| *A61K 31/498* | (2006.01) | |
| *A61K 31/137* | (2006.01) | |
| *A61K 31/4174* | (2006.01) | |
| *A61K 9/00* | (2006.01) | |

(52) U.S. Cl.
CPC .......... *A61K 31/498* (2013.01); *A61K 31/137* (2013.01); *A61K 31/4174* (2013.01); *A61K 9/0019* (2013.01); *A61K 9/0048* (2013.01)

(58) Field of Classification Search
CPC .............. A61K 31/498; A61K 31/137; A61K 31/4174; A61K 9/0019; A61K 9/0048; A61K 45/06; A61P 27/08; A61P 27/00
See application file for complete search history.

(56) References Cited

U.S. PATENT DOCUMENTS

| | | |
|---|---|---|
| 8,445,526 B2 | 5/2013 | Horn |
| 8,999,938 B2 | 4/2015 | Horn |
| 2008/0242733 A1 | 10/2008 | Booth et al. |
| 2013/0345149 A1 | 12/2013 | Warner et al. |
| 2015/0018358 A1 | 1/2015 | Shanler et al. |

FOREIGN PATENT DOCUMENTS

| | | |
|---|---|---|
| WO | 2004010894 A2 | 2/2004 |

OTHER PUBLICATIONS

Alfonso, "Pharmacologic pupillary modulation in the perioperative period", J Cataract Refract Surg—vol. 14(1), Jan. 1988.*
Mojumder et al., "Topical Mydriatics affect Light-Evoked Retinal Responses in anesthetized Mice", Investigative Ophthalmology & Visual Science, Jan. 2010, vol. 51, No. 1, pp. 567-576.
Gherezghiher et al., "Clonidine Mydriasis in the Rat", European Journal of Pharmacology, 57 (1979): 263-266.
Hsu et al., "Effect of Amitraz and Chlordimeform on Heart Rate and Pupil Diameter in Rats: Mediated by a2-Adrenoreceptors", Toxicology and Applied Pharmacology 73, 411-415 (1984).
Koss, "Topical Clonidine Produces Mydriasis by a Central Nervous System Action", European Journal of Pharmacology, 55 (1979): 305-310.
Heck et al., "Differential Down-Regulation of Alpha-2 Adrenergic Receptor Subtypes," Life Sciences, vol. 62, Nos. 17/18, 1998, pp. 1467-1472.
Falzon et al., "Denervation supersensitivity to 1% phenylephrine in Horner syndrome can be demonstrated 10 days after the onset of symptoms," Br J Ophthalmol, Jan. 2009, vol. 93, No. 1, p. 130.
Yousufzai et al., "Alpha1-Adrenergic Receptor Induced Subsensitivity and Supersensitivity in Rabbit Iris-Ciliary Body," Investigative Ophthalmology & Visual Science, Mar. 1987, vol. 28/3, pp. 409-419.
Davies et al., "Increased Numbers of Alpha Receptors in Sympathetic Denervation Supersensitivity in Man," J. Clin. Invest., vol. 69, Apr. 1982, pp. 779-784.
Brown et al., "The Effect of Daily Use of Brimonidine Tartrate on the Dark-adapted Pupil Diameter," Brief Reports, vol. 138, No. 1, 2004, pp. 149-151.
Buckley et al., "Ageing and Alpha1 Adrenoceptors in the Iris," Eye (1987) 1, 211-216.
Cahill et al., "Pupillary autonomic denervation with increasing duration of diabetes mellitus," Br J Ophthalmol, 2001, vol. 95, pp. 1225-1230.
Fleming et al., "Adaptive Supersensitivity," Chapter 9, Catecholamines I, vols. 90-91 of Handbook of Experimental Pharmacology, Springer Science & Business Media, 2012, pp. 509-559.

(Continued)

*Primary Examiner* — Sahar Javanmard
(74) *Attorney, Agent, or Firm* — Polsinelli PC

(57) ABSTRACT

The present invention provides methods for inducing or enhancing rapid and significant dilation of a subject's pupils. In certain embodiments, the method comprises upregulating the alpha-1 receptors in the eye of the subject, thereby increasing sensitivity to alpha-1 agonists. In other embodiments, such upregulation is achieved through administration of at least one compound selected from the group consisting of alpha-2 selective agonists and beta adrenoreceptor antagonists for a period of time prior to the intended time of dilation. After inducing the upregulation of alpha-1 receptors through the administration of at least one compound selected from the group consisting of alpha-2 selective agonists and beta adrenoreceptor antagonists, alpha-1 agonists can be administered to induce or enhance rapid and strong pupil dilation.

26 Claims, 10 Drawing Sheets

(56) References Cited

OTHER PUBLICATIONS

Clark, "Ocular Autonomic Nerve Function in Proliferative Diabetic Retinopathy," Eye (1988), vol. 2, pp. 96-101.

Latif, "Cross Talk between Cyylic AMP and the Polyphosphoinositide Signaling Cascade in Iris Sphincter and Other Nonvascular Smooth Muscle," MINIREVIEW, Proceedings of the Society for Experimental Biology and Medicine, vol. 211, Academic Press, 1996, pp. 163-177.

Datta et al., Ocular and Cardiobascular Autonomic Function in Diabetic Patients with Varying Severity of Retinopathy, Indian J Physiol Pharmacol, 2005, 49(2): 171-178.

Vartiainen et al., "Dexmedetomidine-Induced Ocular Hypotension in Rabbits with Normal or Elevated Intraocular Pressures," Investigative Ophthalmology & Visual Science, May 1992, vol. 33, No. 6, pp. 2019-2023.

Fakhoury et al., "Effect of Topical Dexmedetomidine (0.0055%) on Intraocular Pressure in Healthy Eyes: A Randomized Controlled Trial," Journal of Current Glaucoma Practice, vol. 15, No. 2, May-Aug. 2021, pp. 58-63.

Matsson, "Alpha-1 and Alpha-2-Adrenoreceptors in the Eye, Pharmacological and Functional Characterization," Comprehensive Summaries of Uppsala Dissertations from the Faculty of Medicine, 1058, Uppsala University, 2001, 66 pages.

Huber et al, "Mydriatic drugs for diabetic patients," British Journal of Ophthalmology, 1985, 69, pp. 425-427.

Kirkpatrick et al., "Development of Pupillary Adrenergic Supersensitivity after Pharmacologic Induction of Oculosympathetic Defect," Health Research Abstract Submissions, #10, University of Iowa, College of Medicine, Ophthalmology and Visual Sciences, Mar. 23, 2012, 2 pages.

Koc et al., "Topical Apraclonidine Testing Discloses Pupillary Sympathetic Denervation in Diabetic Patients," J Neuro-Ophthalmol, 2006, vol. 26, No. 1, pp. 25-29.

Potter et al., "Medetomidine-Induced Alterations of Intraocular Pressure and Contraction of the Nictitating Membrane," Investigative Ophthalmology & Visual Science, Sep. 1991, vol. 32, No. 10, pp. 2799-2805.

Merlie et al., "Denervation Supersensitivity in Skeletal Muscle: Analysis with a Cloned cDNA Probe," The Journal of Cell Biology, Jul. 1984, vol. 99, pp. 332-335.

Quintas et al, "Mechanisms of adaptive supersensitivity in vas deferens," Autonomic Neuroscience: Basic and Clinical 146, 2009, pp. 38-46.

Ramsay, Dilute Solutions of Phenylephrine and Pilocarpine in the Diagnosis of Disordered Autonomic Innervation of the Iris, Observations in Normal Subjects, and in the Syndromes of Horner and Holmes-Adie, Journal of the Neurological Sciences, 1986, 73: 125-134.

Smith et al., "Evidence for a neuropathic aetiology in the small pupil of diabetes mellitus," British Journal of Ophthalmology, 1983, 67, 89-93.

MacDonald et al, "Systemic absorption and systemic effects of ocularly administered desmedetomidine in rabbits," Current Eye Research, 1993, vol. 12, No. 5, pp. 451-460.

\* cited by examiner

Normal Eye
Pupil Diameter: 4mm

Treated Eye
Pupil Diameter: 2mm

Phenylephrine 10% administration

Pupil Diameter: 6mm

Pupil Diameter: 8mm

METHODS FOR INDUCING PUPIL DILATION

CROSS-REFERENCE TO RELATED APPLICATIONS

The present application is a 35 U.S.C. § 371 national phase application from, and claims priority to, International Application No. PCT/US2018/059469, filed Nov. 6, 2018, which claims priority under 35 U.S.C. § 119(e) to U.S. Provisional Application No. 62/584,200, filed Nov. 10, 2017, all of which applications are incorporated by reference herein in their entireties.

BACKGROUND OF THE INVENTION

Each year, millions of people suffer from poor pupillary dilation during eye exams and eye surgery. Poor pupil dilation leads to inadequate visualization of pathology by an eye care specialist during clinic-based exams. Even more importantly, the surgical work area of the eye is severely diminished in these patients. Narrowing a surgeon's work area has significant implications for surgical safety and patient outcomes and contributes to higher rates of complications. Capsular rupture is one of the many complications that can occur and is estimated to cost the U.S. up to $35 million annually.

When poor pupil dilation is paired with progressive intraoperative pupillary constriction and billowing of the iris with or without iris prolapse through the surgical wounds, the condition is called intraoperative floppy iris syndrome (IFIS). Multiple comorbidities such as diabetes and hypertension can cause IFIS. However, IFIS occurs most commonly in patients who take medication for benign prostatic hyperplasia (BPH) or ureteral stones. BPH is the most commonly diagnosed condition for male patients age 45-74. It is estimated that up to 90% of men between the age of 45 and 90 suffer from BPH. The most common and effective treatment, recommended as first line therapy for BPH by the American Urological Association, is the selective α-1 blocker (e.g.: tamsulosin, or FLOMAX™) that target α-1 receptors in the genitourinary (GU) system. Unfortunately, α-1 receptors are also found on the iris and control the muscles that cause dilation in the eye. Selective α-1 blockers influence iris dilation and stability long term, even after discontinuation of these medications. The risk of IFIS among men taking tamsulosin was as high as 90% in 10 retrospective and prospective studies.

The scope of the unmet clinical need is staggering. 3.6 million cataract surgeries are performed each year in the USA alone, 20 million worldwide. An estimated 2% of these surgeries have IFIS (72,000 cases each year in the USA). The cataract and BPH population is only expected to worsen over the next 30 years due to population aging.

Another problem regarding pupil dilation is the length of waiting time needed before adequate dilation. Whether in clinic or in the operating room (OR), eye care specialists must wait 20-40 minutes before dilation is achieved. This adds to workflow burden and extends a patient's clinic visit, which has negative implications for clinic flow and decreases patient satisfaction.

Current solutions offer unsatisfactory clinical outcomes. These solutions use progressively-higher concentrations of α-1 receptor agonists to try and "flood" the existing α-1 receptor population. However, this method does not solve the problem of a dysfunctional/depleted α-1 receptor population. Not surprisingly, these pharmacologic solutions only improve pupil dilation marginally and surgeons will typically progress to using mechanical means of enlarging the pupil during surgery. These surgical pupil expansion devices are expensive, add to operating time, increase post-operative inflammation, and prolong recovery due to iris manipulation. Pupil expansion devices can also lead to permanently misshapen pupils post operatively.

Thus, there is a need in the art for compositions and methods that allow for the effective and rapid dilation of pupils in a subject. The present invention meets and addresses these needs.

BRIEF SUMMARY OF THE INVENTION

In one aspect, the invention provides a method of inducing dilation of at least one pupil of a subject. In certain embodiments, the method comprises administering to the subject a therapeutically effective amount of a first composition comprising at least one compound selected from the group consisting of alpha-2 selective agonists and beta adrenoreceptor antagonists, or a salt or solvate thereof. In other embodiments, the method comprises administering to the subject a therapeutically effective amount of a second composition comprising at least one alpha-1 agonist, or a salt or solvate thereof.

In certain embodiments, the first composition comprises at least one compound selected from the group consisting of agmatine, amitraz, apraclonidine, atenolol, bisoprolol, cannabigerol, chloroethylclonidine, clonidine, brimonidine, butoxamine, detomidine, dexmedetomidine, fadolmidine, guanabenz, guanfacine, ICI-118,551, lofexidine, marsanidine, 7-Me-marsanidine, medetomidine, methamphetamine, metoprolol, mivazerol, nebivolol, 4-NEMD, propranolol, rilmenidine, romifidine, SR 59230A, talipexole, tiamenidine, timolol, tizanidine, tolonidine, vortioxetine, xylazine, and xylometazoline, and any salts and solvates thereof. In other embodiments, the first composition comprises brimonidine. In yet other embodiments, the first composition comprises dexmedetomidine. In yet other embodiments, the first composition comprises at least one compound selected from the group consisting of alpha-2 selective agonists and beta adrenoreceptor antagonists at a concentration ranging from about 0.001% to about 50% (v/v).

In certain embodiments, the second composition comprises at least one compound selected from the group consisting of cirazoline, epinephrine, etilefrine, metaraminol, methoxamine, midodrine, naphazoline, norepinephrine, oxymetazoline, phenylephrine, pseudoephedrine, tetrahydrozoline, synephrine, and xylometazoline, and any salts and solvates thereof. In other embodiments, the second composition comprises phenylephrine. In yet other embodiments, the second composition comprises at least one alpha-1 agonist at a concentration ranging from about 0.001% to about 50% (v/v).

In certain embodiments, the second composition is administered after the first composition. In other embodiments, the second composition is administered to the subject after a period of time ranging from about 1 hour to about 30 days after administration of the first composition. In yet other embodiments, the second composition is administered to the subject after a period of time ranging from about 1 day to about 10 days. In yet other embodiments, the first composition is administered to the subject two or more times before the second composition is administered. In certain embodiments, the first composition is administered once per day for about 1 day to about 10 days.

In certain embodiments, the first composition is a pharmaceutical composition formulated for topical administration. In other embodiments, the first composition is a pharmaceutical composition formulated for topical administration to the eye of a subject. In yet other embodiments, the first composition is a pharmaceutical composition formulated in a form selected from the group consisting of an ophthalmic drop, ophthalmic ointment, ophthalmic gel, ophthalmic spray, and ophthalmic lotion.

In certain embodiments, the second composition is a pharmaceutical composition formulated for topical administration. In other embodiments, the second composition is a pharmaceutical composition formulated for topical administration to the eye of a subject. In yet other embodiments, the second composition is a pharmaceutical composition formulated in a form selected from the group consisting of an ophthalmic drop, ophthalmic ointment, ophthalmic gel, ophthalmic spray, ophthalmic lotion, and ophthalmic intracameral injection.

In certain embodiments, the first composition and the second composition are administered to the subject topically or through intracameral injection. In other embodiments, the first composition and the second composition are administered directly to at least one portion of the eye of the subject. In yet other embodiments, the first composition and the second composition are administered to the subject directly to the cornea, iris, sclera, or anterior chamber of the subject.

In another aspect, the invention provides a kit comprising a therapeutically effective amount of a first composition comprising at least one compound selected from the group consisting of alpha-2 selective agonists and beta adrenoreceptor antagonists; and a therapeutically effective amount of a second composition comprising at least one alpha-1 agonist.

In certain embodiments, the first composition of the kit comprises at least one compound selected from the group consisting of agmatine, amitraz, apraclonidine, atenolol, bisoprolol, cannabigerol, chloroethylclonidine, clonidine, brimonidine, butoxamine, detomidine, dexmedetomidine, fadolmidine, guanabenz, guanfacine, ICI-118,551, lofexidine, marsanidine, 7-Me-marsanidine, medetomidine, methamphetamine, metoprolol, mivazerol, nebivolol, 4-NEMD, propranolol, rilmenidine, romifidine, SR 59230A, talipexole, tiamenidine, timolol, tizanidine, tolonidine, vortioxetine, xylazine, and xylometazoline, or a salt or solvate thereof.

In certain embodiments, the second composition of the kit comprises at least one compound selected from the group consisting of cirazoline, epinephrine, etilefrine, metaraminol, methoxamine, midodrine, naphazoline, norepinephrine, oxymetazoline, phenylephrine, pseudoephedrine, tetrahydrozoline, synephrine, and xylometazoline, or a salt or solvate thereof.

In certain embodiments, the kit comprises at least two doses of the first composition. In certain embodiments, the kit comprises at least two doses of the second composition.

In certain embodiments, the kit further comprises instructional materials containing instructions for performing the methods of the invention.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 5A shows prior to treatment with any medication and FIG. 5B shows after treatment with phenylephrine hydrochloride 10% to both eyes. Photopic conditions are represented by the boxed areas of the graphs. The horizontal axis tracks time while the vertical axis tracks pupil size.

FIG. 6A shows after treatment with brimonidine tartrate 0.15% to the right eye only, FIG. 6B shows after treatment with phenylephrine 2.5% to both eyes and FIG. 6C shows after treatment with phenylephrine 10% to both eyes. Photopic conditions are represented by the boxed areas of the graphs. The horizontal axis tracks time while the vertical axis tracks pupil size.

FIG. 7A shows after treatment with apraclonidine 0.5% to the right eye only and FIG. 7B shows after treatment with phenylephrine 10% to both eyes. Photopic conditions are represented by the boxed areas of the graphs. The horizontal axis tracks time while the vertical axis tracks pupil size.

FIG. 8A shows before any treatment was administered, FIG. 8B shows after Dexmedetomidine 0.1% was administered to the right eye only and FIG. 8C shows after treatment with phenylephrine 10% to both eyes. Photopic conditions are represented by the boxed areas of the graphs. The horizontal axis tracks time while the vertical axis tracks pupil size.

DETAILED DESCRIPTION OF THE INVENTION

The present invention provides methods for inducing rapid and significant dilation of a patient's pupils. In certain embodiments, the method comprises upregulating the alpha-1 receptors in at least one eye of the subject through administration of at least one compound selected from the group consisting of alpha-2 selective agonists and beta adrenoreceptor antagonists for a period of time prior to the intended time of dilation. In certain embodiments, upregulating the alpha-1 receptors in the at least one eye of the subject increases sensitivity of the at least one eye to alpha-1 agonists. After inducing the upregulation of alpha-1 receptors according to the methods of the invention, alpha-1 agonists can be administered to the pre-treated eye(s) to induce rapid and significant pupil dilation.

Figure 1:
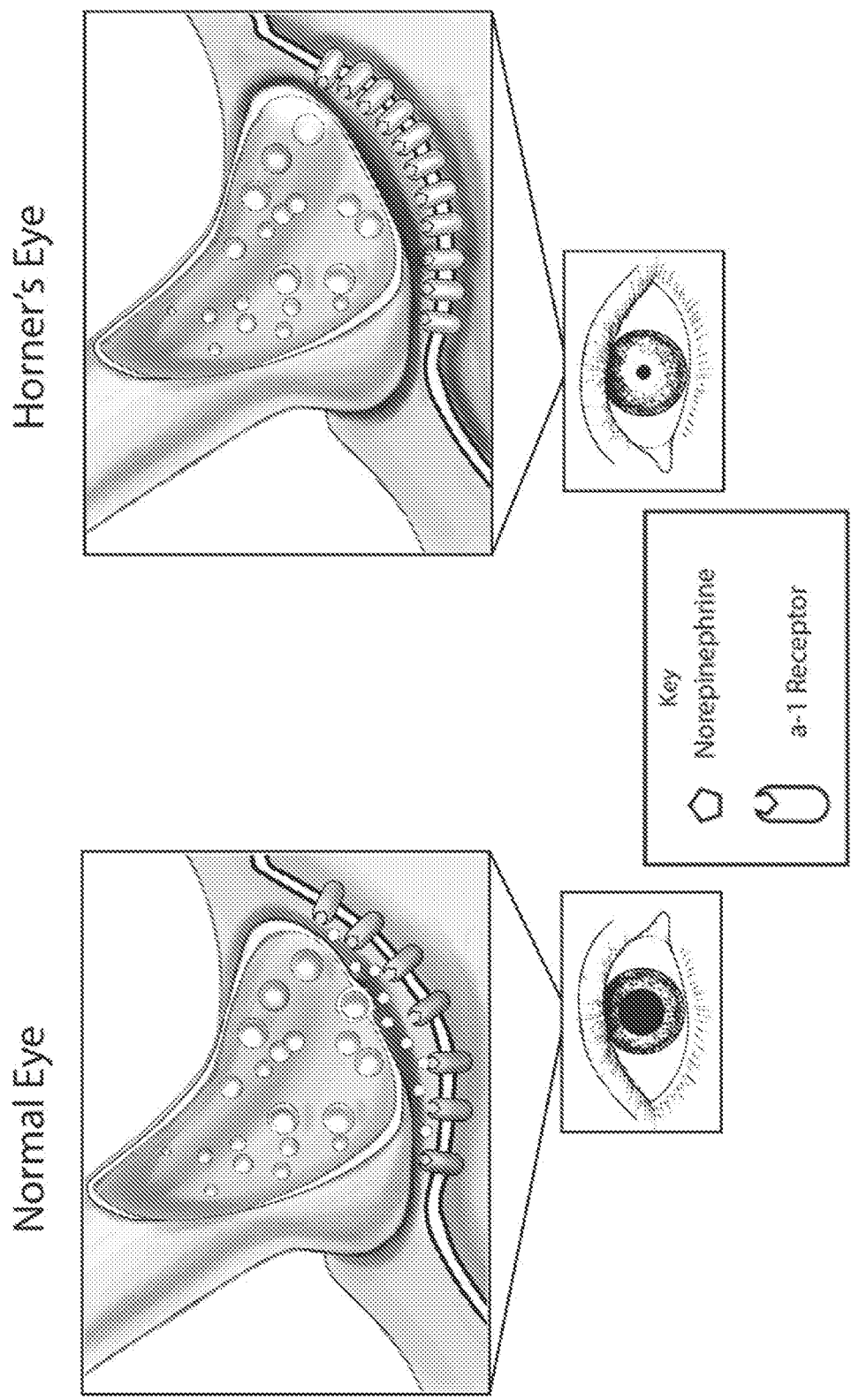
FIG. 1 is a diagram comparing a normal eye to an eye suffering from Horner's Syndrome. The iris is covered in specific types of receptors called α-1 receptors. These receptors respond to norepinephrine resulting in dilation of the pupil. In a normal physiologic state, there is a set level of norepinephrine released that serves to keep the population of α-1 receptors at a normal level. In diseased states, however, there is a lack of norepinephrine release (ex: Horner's Syndrome). This leads to low binding rate of norepinephrine to the iris α-1 receptors. Consequently, the α-1 receptors are upregulated on the iris surface, creating a supersensitive environment for pupil dilation in the event that an α-1 receptor agonist, such as norepinephrine, is released. The left diagram shows a normal eye expressing normal levels of α-1 receptors and the right diagram shows an eye suffering from Horner's syndrome, overexpressing α-1 receptors, and therefore demonstrating super-sensitivity to norepinephrine.
Figure 2:
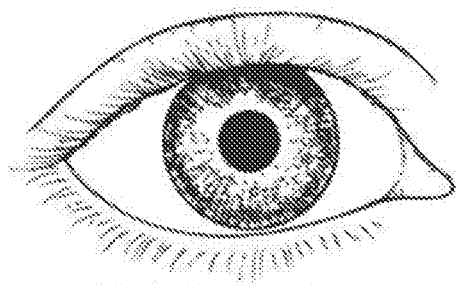
FIG. 2 is a diagram comparing a normal eye to an eye suffering from Horner's Syndrome, before and after treatment with a strong α-2 agonist (Apraclonidine). Since Horner's Syndrome is a unilateral disease that results in loss of sympathetic innervation to the eye, only one eye results in a constricted pupil and upregulation of the α-1 receptors. Apraclonidine is a very weak α-1 agonist and strong α-2 agonist. Because of the weak α-1 agonist activity, apraclonidine does not have any significant effect on pupil dilation when placed on the healthy eye of a Horner's Syndrome patient. However, when apraclonidine is placed on the diseased eye lacking normal sympathetic innervation, apraclonidine saturates all of the α-1 receptors on the supersensitive iris and creates a dramatic dilation.
Figure 2:
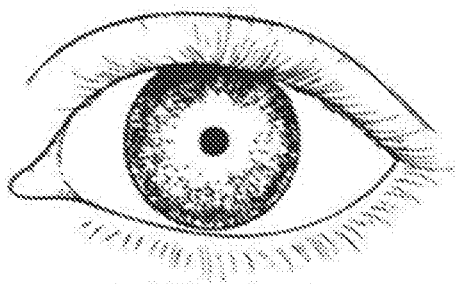
Figure 2:
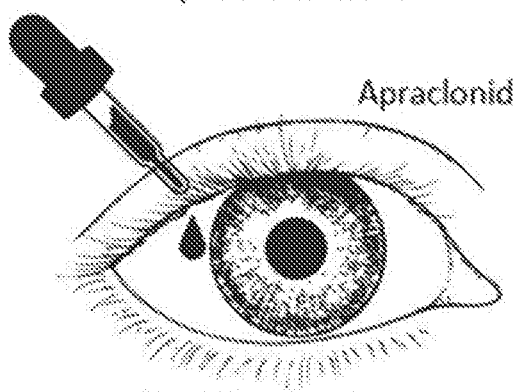
Figure 2:
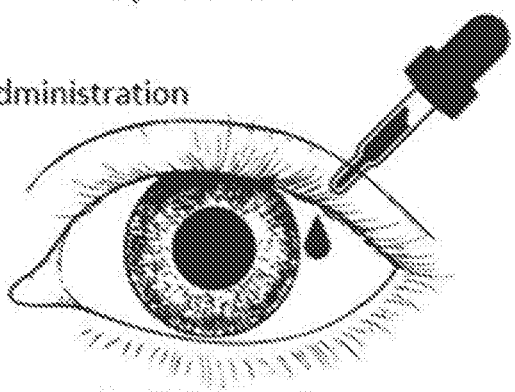

Without intending to be limited to any particular theory or mechanism, the methods of the invention utilize the law of denervation supersensitivity (Cannon's Law), whereby a tissue deprived of its normal nerve supply will develop hypersensitivity to its own neurotransmitter(s). One example is the unilateral disease Horner's syndrome, in which the sympathetic innervation to the iris dilator muscle is disrupted, thus leading to a smaller, constricted pupil compared to the other normal eye. Lack of sympathetic stimulation to the iris for 2 to 5 days leads to supersensitivity of the iris dilator muscle via upregulation of α-1 receptors (FIG. 1). Ophthalmologists employ this supersensitivity to diagnose Horner's Syndrome using a weak α-1 agonist, apraclonidine. The normal pupil will not constrict when exposed to such a weak α-1 agonist, but the Horner's pupil has a much greater population of α-1 receptors and will dilate briskly in response to apraclonidine (FIG. 2).

Figure 3:
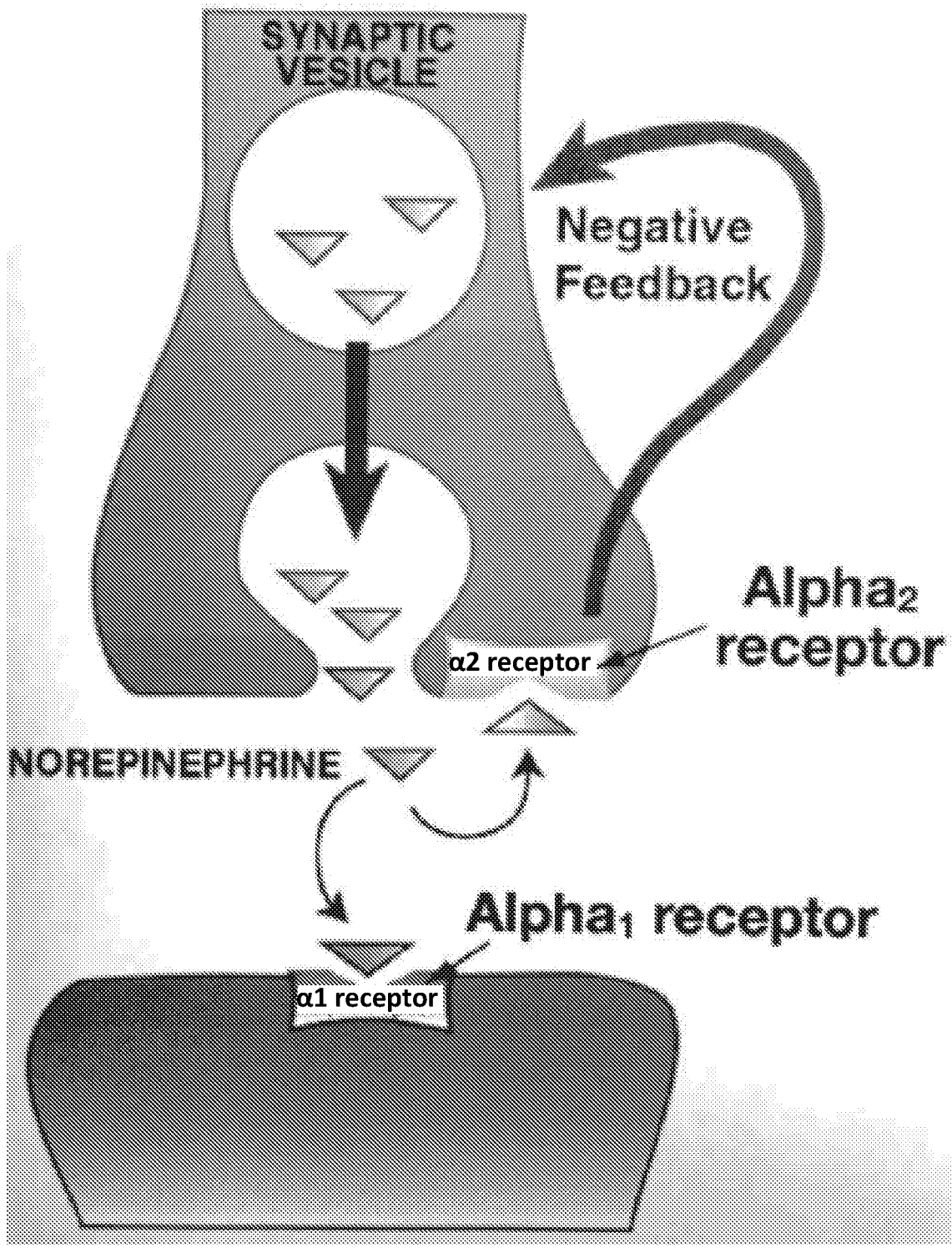
FIG. 3 is a diagram demonstrating a pharmacological mechanism by which Horner's Syndrome can be induced in a patient. Substantially, the method induces Horner's Syndrome-like symptoms by taking advantage of the negative feedback loops that exist within the synapse of the sympathetic nerve endings. α-1 receptors are found at the postsynaptic cells to create pupil dilation in the event of norepinephrine binding. α-2 receptors are found in the presynaptic cells and work in a negative feedback loop. By applying topical α-2 agonists to the eye, the negative feedback loop is constantly turned "on", thus limiting norepinephrine release. This pharmacologic mimicry of Horner's Syndrome results in a lack of norepinephrine in the synaptic cleft and leads to upregulation of α-1 receptors on the iris surface.
Figure 4:
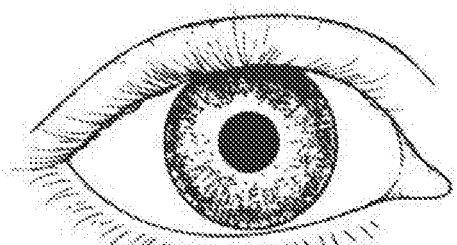
FIG. 4 is a diagram comparing a normal eye to an eye treated with a strong α-2 agonist, before and after treatment with a α-1 agonist (phenylephrine). Once an α-1 receptor supersensitive environment is created on the iris, any α-1 agonist (ex: phenylephrine) can be used to dilate the pupil much more effectively.
Figure 4:
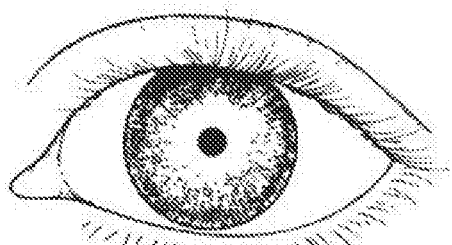
Figure 4:
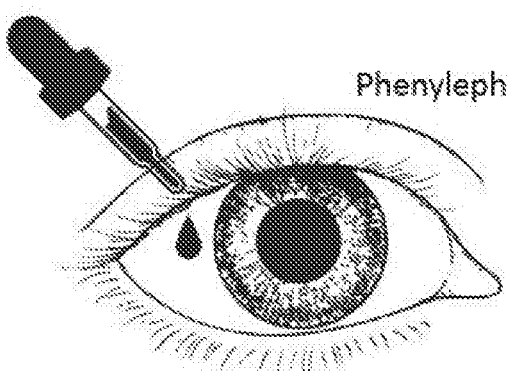
Figure 4:
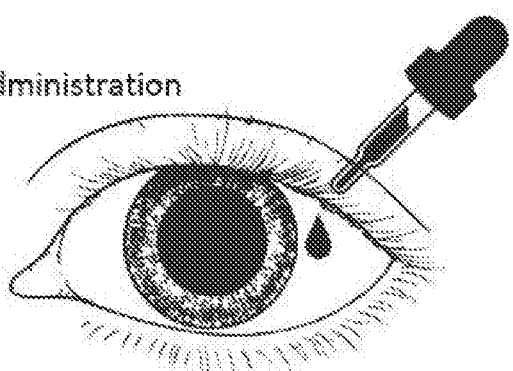

Through disease mimicry, the therapy of the invention uses topical α-2 agonists to induce a pharmacological Horner's Syndrome. Since activation of pre-synaptic α-2 receptors activates the negative feedback mechanism, this decreases the release of norepinephrine (NE) into the synaptic cleft (FIG. 3). The lack of NE in the synaptic cleft upregulates the post-synaptic α-1 receptors on the iris dilator muscle, which in turn results in supersensitivity to any topical α-1 receptor agonist such as phenylephrine or epinephrine (FIG. 4).

By inducing iris supersensitivity through the law of denervation supersensitivity, it is possible to increase responsiveness to dilation medication leading to improved pupillary dilation. One method of doing this is through use of an α-2 agonist. Theoretically, the higher the α-2 affinity of a compound, the more effective the compound is at inducing supersensitivity and increasing pupillary dilation when dilation medication is administered. Without intending to be limited to any particular theory, compounds with a higher α2:α1 affinity ratio may work better than compounds with a lower α2:α1 affinity ratio. Furthermore, lower α2:α1 affinity ratio compounds could theoretically impede dilation since the α-1 activity could cause a decrease in iris sensitivity, leading to decreased response to dilation medication. Experiments were undertaken as a proof of concept for this theory using 3 compounds: apraclonidine, brimonidine tartrate, and dexmedetomidine. See Table 1 for α2:α1 affinity of some exemplary compounds.

TABLE 1

Affinities for α receptors in the different compounds tested

| Compound | α2:α1 affinity |
| --- | --- |
| Apraclonidine | 150 |
| Brimonidine | 976 |
| Dexmedetomidine | 1620 |

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in pharmacology and ophthalmology are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject or individual is a human. Non-human subjects include, for example, livestock and pets, such as ovine, bovine, porcine, canine, feline, equine and murine mammals.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: BAK, benzalkonium chloride; BPH, benign prostatic hyperplasia; CAPB, cocamidopropyl betaine; EDTA, ethylenediaminetetraacetic acid; IFIS, intraoperative floppy iris syndrome; NE, norepinephrine.

Methods

The invention provides a method of inducing dilation in at least one pupil of a subject. In certain embodiments, the method comprises administering to the subject a therapeutically effective amount of at least one first compound selected from the group consisting of alpha-2 selective agonists and beta adrenoreceptor antagonists. In other embodiments, the method comprises administering to the subject a therapeutically effective amount of at least one alpha-1 agonist.

In certain embodiments, the at least one first compound is selected from the group consisting of agmatine, amitraz, apraclonidine, atenolol, bisoprolol, cannabigerol, chloroethylclonidine, clonidine, brimonidine, butoxamine, detomidine, dexmedetomidine, fadolmidine, guanabenz, guanfacine, ICI-118,551, lofexidine, marsanidine, 7-Memarsanidine, medetomidine, methamphetamine, metoprolol, mivazerol, nebivolol, 4-NEMD, propranolol, rilmenidine, romifidine, SR 59230A, talipexole, tiamenidine, timolol, tizanidine, tolonidine, vortioxetine, xylazine, and xylometazoline and any salts and solvates thereof. In other embodiments, the at least one first compound comprises any known or yet undiscovered alpha-2 agonist and/or beta adrenoreceptor antagonist. In yet other embodiments, the at least one first compound is/comprises brimonidine. In yet other embodiments, the at least one first compound is/comprises dexmedetomidine.

In certain embodiments, the at least one first compound has an $\alpha2{:}\alpha1$ affinity ratio equal to or greater than about 150. In certain embodiments, the at least one first compound has an $\alpha2{:}\alpha1$ affinity ratio equal to or greater than about 200. In certain embodiments, the at least one first compound has an $\alpha2{:}\alpha1$ affinity ratio equal to or greater than about 250. In certain embodiments, the at least one first compound has an $\alpha2{:}\alpha1$ affinity ratio equal to or greater than about 300. In certain embodiments, the at least one first compound has an $\alpha2{:}\alpha1$ affinity ratio equal to or greater than about 400. In certain embodiments, the at least one first compound has an $\alpha2{:}\alpha1$ affinity ratio equal to or greater than about 500. In certain embodiments, the at least one first compound has an $\alpha2{:}\alpha1$ affinity ratio equal to or greater than about 600. In certain embodiments, the at least one first compound has an $\alpha2{:}\alpha1$ affinity ratio equal to or greater than about 700. In certain embodiments, the at least one first compound has an $\alpha2{:}\alpha1$ affinity ratio equal to or greater than about 800. In certain embodiments, the at least one first compound has an $\alpha2{:}\alpha1$ affinity ratio equal to or greater than about 900. In certain embodiments, the at least one first compound has an $\alpha2{:}\alpha1$ affinity ratio equal to or greater than about 1000.

In certain embodiments, the at least one alpha-1 agonist is selected from the group consisting of cirazoline, epinephrine, etilefrine, metaraminol, methoxamine, midodrine, naphazoline, norepinephrine, oxymetazoline, phenylephrine, pseudoephedrine, tetrahydrozoline, synephrine, and xylometazoline. In other embodiments, the at least one alpha-1 agonist is any known or yet undiscovered alpha-1 agonist. In yet other embodiments, the at least one alpha-1 agonist is/comprises phenylephrine.

In certain embodiments, the at least one alpha-1 agonist is administered after the first compound. In other embodiments, the at least one alpha-1 agonist is administered to the subject after a period of time ranging from about 1 hour to about 30 days after administration of the first compound.

In certain embodiments, the first compound is administered to the subject one or more times before the at least one alpha-1 agonist is administered. In other embodiments, the first compound is administered at least once per day for about 1 day to about 10 days prior to the administration of the at least one alpha-1 agonist.

In certain embodiments, the first compound is part of a pharmaceutical composition formulated for topical administration. In other embodiments, the first compound is a pharmaceutical composition formulated for topical administration to the eye of a subject. In certain embodiments, the at least one alpha-1 agonist is part of a pharmaceutical composition formulated for topical administration. In other embodiments, the at least one alpha-1 agonist is part of a pharmaceutical composition formulated for topical administration to the eye of a subject. In other embodiments, the at least one alpha-1 agonist is part of a pharmaceutical composition formulated for intracameral administration.

In certain embodiments, any compound contemplated within the invention can be formulated for topical administration in a topical ophthalmic pharmaceutical composition. In other embodiments, any compound contemplated within the invention can be formulated as part of an ophthalmic drop, ophthalmic ointment, ophthalmic gel, ophthalmic spray, ophthalmic lotion, ophthalmic intracameral medication, or in any other form which would be readily apparent to a person of ordinary skill in the art.

In certain embodiments, the topical ophthalmic pharmaceutical compositions further comprise at least one preservative or additive suitable for ophthalmic administration. In other embodiments, the topical ophthalmic pharmaceutical compositions further comprise at least one compound or a salt or solvate thereof, selected from the group consisting of benzalkonium chloride (BAK), ethylenediaminetetraacetic acid (EDTA), cocamidopropyl betaine (CAPB), sodium laurel sulfate, captisol, citric acid, polyvinyl alcohol, sodium chloride, sodium citrate, purified water, Hydrochloric acid, sodium hydroxide, poloxamer, carboxymethylcelulose, methylcellulose, hyaluronic acid, hydroxymethyl celulose, hydroxypropylmethylcelulose, hydroxyethylcellulose, polyethyleneglycol, dextran, acacia, gelatin, chitosan, povidone, alginic acid, guargum, Veegum, carbopol, locust65 beangum, acidicpolycarbophil, dextran, pectin, polyvinyl pyrridone, hypotonic salt, mesylate, fumarate, acetate, succinate, phosphate, maleate, tartrate, benzoate, carbonate, pamoate, sulfate, bisulfate, hydrobromide, bromide and propyl paraben. In yet other embodiments, additives to the topical ophthalmic pharmaceutical compositions can modify at least one property of the composition selected from the group consisting of lipophilicity, pH, tonicity, solubility, and viscosity.

In certain embodiments, the pharmaceutical composition comprising the at least one first compound comprises about 0.001% to about 50% (v/v) of the at least one first compound. In certain embodiments, the pharmaceutical composition comprising the at least one alpha-1 agonist comprises about 0.001% to about 50% (v/v) of the at least one alpha-1 agonist. In certain embodiments, the pharmaceutical composition comprises about 0.05% (v/v) to about 0.5% (v/v) brimonidine tartrate, more preferably about 0.1% (v/v) to about 0.2% (v/v) brimondine tartrate. In certain embodiments, the pharmaceutical composition comprises about 0.01% (v/v) to about 0.5% (v/v) dexmetomidine, more preferably about 0.01% (v/v) to about 0.1% (v/v) dexmetomidine.

In certain embodiments, any pharmaceutical composition contemplated within the invention have a pH ranging from about pH 4 to about pH 10. In other embodiments the pharmaceutical compositions have a pH of about pH 5 to about pH 7. Without wishing to be limited to any particular theory, the efficacy of an ophthalmic pharmaceutical composition of the invention can be dependent on the composition pH. A person of ordinary skill in the art would be able to determine the optimal pH without undue experimentation.

In certain embodiments, the compounds or compositions contemplated within the invention are administered directly to at least one portion of the eye of the subject. In certain embodiments, the compounds or compositions contemplated within the invention are administered directly to the cornea, iris or sclera to the subject. In certain embodiments, the compounds or compositions contemplated within the invention are administered intracamerally to eye of the subject. In other embodiments, the compounds or compositions contemplated within the invention are administered intravitreally to eye of the subject.

In certain embodiments, the methods of the invention induce upregulation of adrenergic receptors on the surface of the iris of a subject. In certain embodiments, the methods induce upregulation of alpha adrenergic receptors. In other embodiments, the methods induce upregulation of alpha-1 adrenergic receptors.

In certain embodiments, the induced upregulation of alpha adrenergic receptors is temporary and is returned to normal levels after administration of the first composition has been discontinued for a period of time. In other embodiments, the methods of the invention cause no long term side effects.

Without wishing to be limited to any particular theory, the methods of the invention operate through the Law of Denervation Supersensitivity (Cannon's law), whereby a tissue deprived of its normal nerve supply will develop supersensitivity to its own neurotransmitter(s). By administering alpha adrenergic receptor agonists or competitive antagonists to the eye for an extended period of time, the eye becomes more sensitive to alpha-1 adrenergic agonists and beta adrenergic agonists. Once an alpha-1 agonist is administered to an eye that has been pretreated with alpha adrenergic receptor agonists or competitive antagonists, the eye is expected to experience a stronger response than an eye that has not been pretreated.

In certain embodiments, the subject is a mammal. In other embodiments, the subject is a human.

Kits

The invention further provides a kit comprising a therapeutically effective amount of at least one first compound selected from the group consisting of alpha-2 selective agonists and beta adrenoreceptor antagonists; and a therapeutically effective amount of at least one alpha-1 agonist.

In certain embodiments, the at least one first compound is selected from the group consisting of agmatine, amitraz, apraclonidine, atenolol, bisoprolol, cannabigerol, chloroethylclonidine, clonidine, brimonidine, butoxamine, detomidine, dexmedetomidine, fadolmidine, guanabenz, guanfacine, ICI-118,551, lofexidine, marsanidine, 7-Me-marsanidine, medetomidine, methamphetamine, metoprolol, mivazerol, nebivolol, 4-NEMD, propranolol, rilmenidine, romifidine, SR 59230A, talipexole, tiamenidine, timolol, tizanidine, tolonidine, vortioxetine, xylazine, and xylometazoline. In other embodiments, the at least one first compound comprises any known or yet undiscovered alpha-2 agonist and/or beta adrenoreceptor antagonist. In yet other embodiments, the at least one first compound is/comprises brimonidine.

In certain embodiments, the at least one alpha-1 agonist is selected from the group consisting of cirazoline, epinephrine, etilefrine, metaraminol, methoxamine, midodrine, naphazoline, norepinephrine, oxymetazoline, phenylephrine, pseudoephedrine, tetrahydrozoline, synephrine, and xylometazoline. In other embodiments, the at least one alpha-1 agonist is any known or yet undiscovered alpha-1 agonist. In yet other embodiments, the at least one alpha-1 agonist is/comprises phenylephrine.

In certain embodiments, the kit comprises at least two doses of the at least one first compound, which is optionally formulated as a pharmaceutical composition. In other embodiments, the kit comprises at least two doses of the at least one alpha-1 agonist, which is optionally formulated as a pharmaceutical composition.

In certain embodiments, the kit further comprises instructional materials containing instructions for performing the methods of the invention.

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Molecules of the invention may be isolated as crystalline or amorphous free bases. Such crystalline or amorphous free bases may be obtained directly during the processing step wherein the final amine is attached during the synthetic process, and may also or alternatively be obtained by separately dissolving and crystallizing, and/or precipating, the free base from a suitable solvent or mixture of solvents. Suitable solvents may include, but are not limited to, MeCN, MEK, MIBK, EtOAc, iPrOAc, water, heptane, MTBE, cyclohexane, toluene, MeOH, EtOH, n-PrOH, IPA, nBuOH, 2-BuOH, isoamyl alcohol, and THF.

Combination and Concurrent Therapies

In one embodiment, the compositions of the invention are useful in the methods of present invention when used concurrently or in combination with at least one additional compound useful for preventing and/or treating diseases and/or disorders related to eye health.

These additional compounds may comprise compounds of the present invention or other compounds, such as commercially available compounds, known to treat, prevent, or reduce the symptoms of diseases and/or disorders related to eye health. In certain embodiments, the combination of at least one compound of the invention or a salt thereof, and at least one additional compound useful for preventing and/or treating diseases and/or disorders related to eye health, has additive, complementary or synergistic effects in the prevention and/or treatment of diseases and/or disorders related to eye health.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the compound and the agent are physically mixed in the composition. In another embodiment, the compound and the agent are physically separated in the composition.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to yield the desired effects. An effective amount of the therapeutic compound necessary to achieve a therapeutic effect may vary according to factors such as the health of the patient; the age, sex, and weight of the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutically effective amount or dose of a compound of the present invention depends on the age, sex and weight of the patient and the current medical condition of the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 300 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In certain embodiments, the compositions of the invention are administered for as little as 1 day or for as long as 10 days or more. In other embodiments, the compositions are administered at least once per day, at least twice per day, at least four times per day, at least eight times per day or any frequencies between.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In one embodiment, the present invention is directed to a packaged pharmaceutical composition comprising a container holding a therapeutically effective amount of a compound of the invention, alone or in combination with a second pharmaceutical agent; and instructions for using the compound to carry out the methods of the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Test compounds were procured from the following sources and used without further purification or processing unless otherwise noted: Apraclonidine 0.5% (Alcon Laboratories); Brimonidine tartrate 0.15% (Allergan); Dexmedetomidine 0.1% (compounded using dexmedetomidine 0.1%; along with other components commonly found in eye medications: BAK, EDTA, CAPB, sodium laurel sulfate, captisol, and sodium chloride). Dilation medication used was Phenylephrine hydrochloride 10% (Akorn, Inc). Pupillometer used was a Neuroptics DP-2000 Binocular Pupillometer).

Experimental Procedures

Control

Dilation using phenylephrine hydrochloride 10% was conducted in both eyes of the test subject to use as a control against the other compounds being tested. See FIGS. 5A-5B and Tables 2-3.

TABLE 2

Figure 5A:
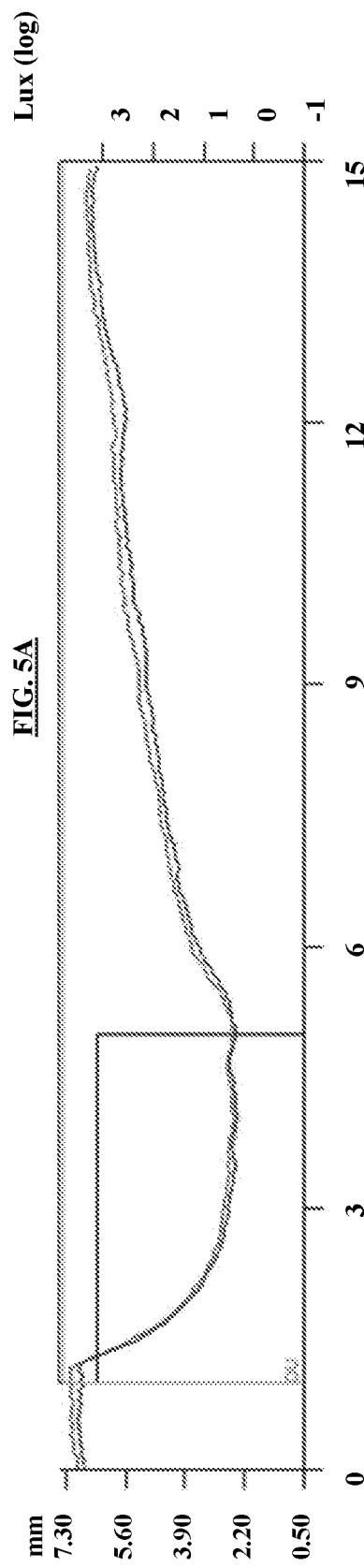
FIGS. 5A-5B are graphs showing pupil dilation during a control experiment where a subject was treated only with phenylephrine hydrochloride 10%.

| Data derived from FIG. 5A | | | | | | |
|---|---|---|---|---|---|---|
| | Right | Left | RPupil Ave | LPupil Ave | RStim Ave | LStim Ave |
| Max (mm) | 7.19 | 6.88 | 7.19 | 6.88 | 7.03 | 7.03 |
| Min (mm) | 2.51 | 2.44 | 2.51 | 2.44 | 2.47 | 2.47 |
| DELTA (mm) | 4.68 | 4.44 | 4.68 | 4.44 | 4.56 | 4.56 |
| CH (%) | 65 | 65 | 65 | 65 | 65 | 65 |
| CLAT (s) | 0.19 | 0.24 | 0.19 | 0.24 | 0.22 | 0.22 |
| CV (mm/s) | 1.55 | 1.53 | 1.55 | 1.53 | 1.54 | 1.54 |
| MCV (mm/s) | 6.43 | 6.53 | 6.43 | 6.53 | 6.48 | 6.48 |
| DV (mm/s) | 1.06 | 0.70 | 1.06 | 0.70 | 0.88 | 0.88 |

TABLE 3

Figure 5B:
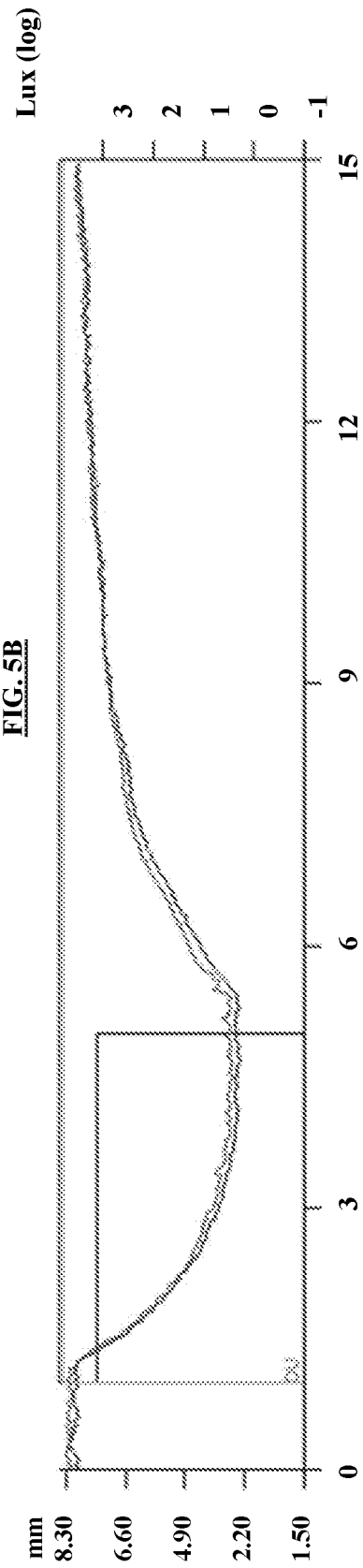

| Data derived from FIG. 5B | | | | | | |
|---|---|---|---|---|---|---|
| | Right | Left | RPupil Ave | LPupil Ave | RStim Ave | LStim Ave |
| Max (mm) | 8.21 | 8.01 | 8.21 | 8.01 | 8.11 | 8.11 |
| Min (mm) | 3.59 | 3.36 | 3.59 | 3.36 | 3.48 | 3.48 |
| DELTA (mm) | 4.62 | 4.65 | 4.62 | 4.65 | 4.63 | 4.63 |
| CH (%) | 56 | 58 | 56 | 58 | 57 | 57 |
| CLAT (s) | 0.20 | 0.24 | 0.20 | 0.24 | 0.22 | 0.22 |
| CV (mm/s) | 1.35 | 1.29 | 1.35 | 1.29 | 1.32 | 1.32 |
| MCV (mm/s) | 4.46 | 4.78 | 4.46 | 4.78 | 4.62 | 4.62 |
| DV (mm/s) | 1.45 | 1.40 | 1.45 | 1.40 | 1.43 | 1.43 |

Experiment 1

Brimonidine tartrate 0.15% was administered in the right eye of the test subject three (3) times a day for 4 days. After this, dilation using phenylephrine hydrochloride 2.5% or phenylephrine hydrochloride 10% was conducted to investigate the effects of the compound on pupil dilation. See FIGS. 6A-6B and Tables 4-5.

TABLE 4

Figure 6A:
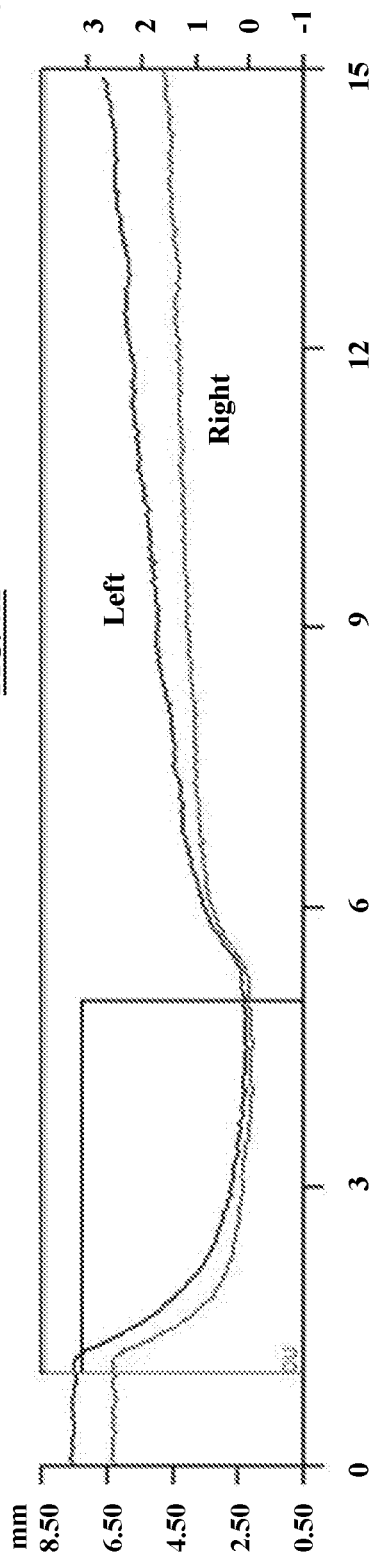
FIGS. 6A-6C are graphs showing pupil dilation wherein the right eye of the subject was administered brimonidine tartrate 0.15% three (3) times a day for 4 days and then administered phenylephrine hydrochloride 2.5% or 10%.

| Data derived from FIG. 6A | | | | | | |
|---|---|---|---|---|---|---|
| | Right | Left | RPupil Ave | LPupil Ave | RStim Ave | LStim Ave |
| Max (mm) | 6.27 | 7.46 | 6.27 | 7.46 | 6.86 | 6.86 |
| Min (mm) | 2.06 | 2.25 | 2.06 | 2.25 | 2.16 | 2.16 |
| DELTA (mm) | 4.21 | 5.21 | 4.21 | 5.21 | 4.70 | 4.70 |
| CH (%) | 67 | 70 | 67 | 70 | 69 | 69 |
| CLAT (s) | 0.18 | 0.17 | 0.18 | 0.17 | 0.17 | 0.17 |
| CV (mm/s) | 1.21 | 1.53 | 1.21 | 1.53 | 1.37 | 1.37 |
| MCV (mm/s) | 6.76 | 6.38 | 6.76 | 6.38 | 6.57 | 6.57 |
| DV (mm/s) | 1.00 | 1.05 | 1.00 | 1.05 | 1.02 | 1.02 |

TABLE 5

Figure 6B:
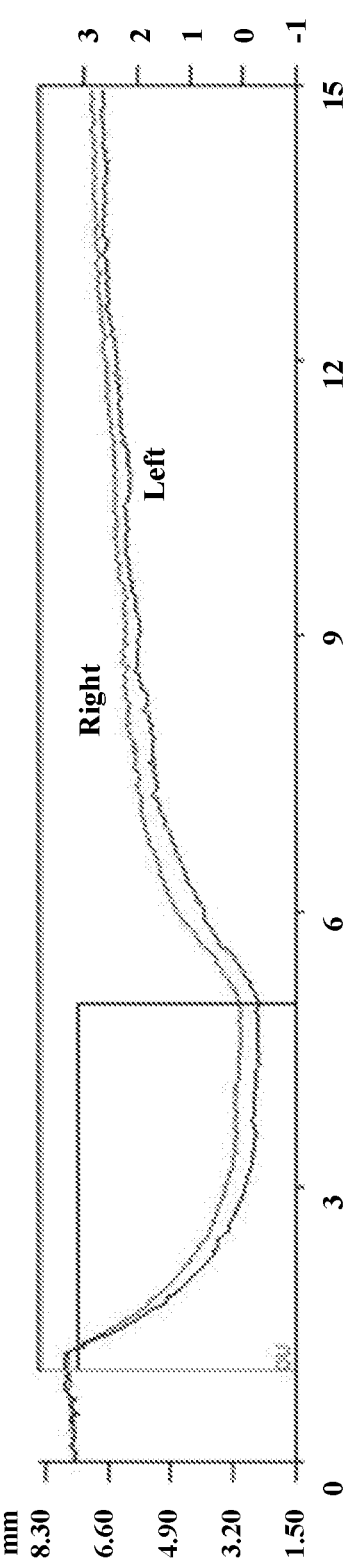

Data derived from FIG. 6B

|  | Right | Left | RPupil Ave | LPupil Ave | RStim Ave | LStim Ave |
|---|---|---|---|---|---|---|
| Max (mm) | 7.69 | 7.77 | 7.69 | 7.77 | 7.73 | 7.73 |
| Min (mm) | 2.99 | 2.51 | 2.99 | 2.51 | 2.75 | 2.75 |
| DELTA (mm) | 4.70 | 5.26 | 4.70 | 5.26 | 4.98 | 4.98 |
| CH (%) | 61 | 68 | 61 | 68 | 64 | 64 |
| CLAT (s) | 0.19 | 0.19 | 0.19 | 0.19 | 0.19 | 0.19 |
| CV (mm/s) | 1.30 | 1.61 | 1.30 | 1.61 | 1.46 | 1.46 |
| MCV (mm/s) | 5.40 | 6.71 | 5.40 | 6.71 | 6.06 | 6.06 |
| DV (mm/s) | 1.39 | 1.33 | 1.39 | 1.33 | 1.36 | 1.36 |

TABLE 6

Figure 6C:
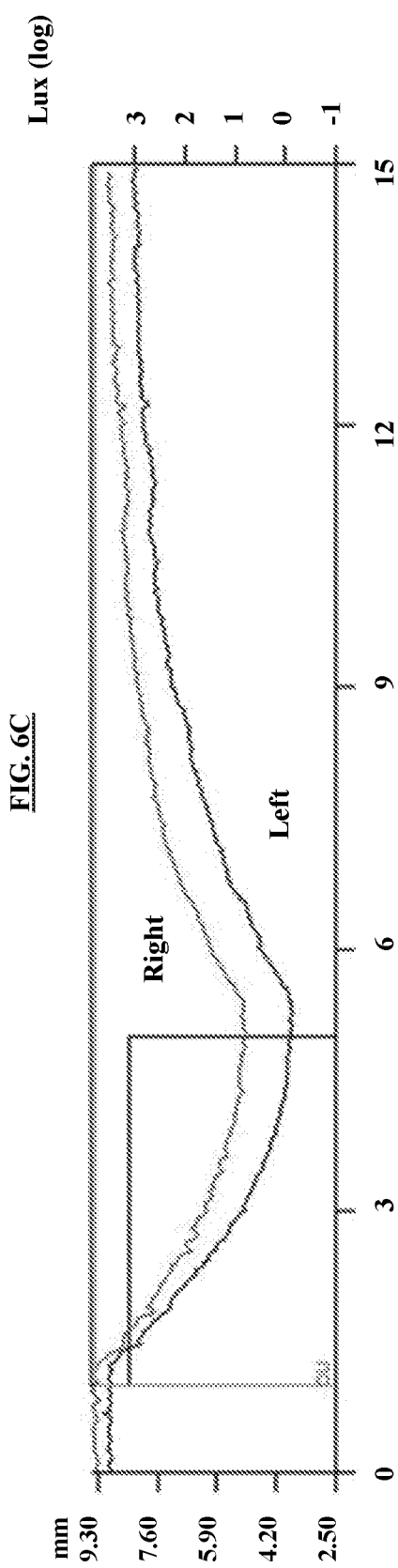

Data derived from FIG. 6C

|  | Right | Left | RPupil Ave | LPupil Ave | RStim Ave | LStim Ave |
|---|---|---|---|---|---|---|
| Max (mm) | 9.40 | 8.96 | 9.40 | 8.96 | 9.18 | 9.18 |
| Min (mm) | 5.12 | 3.77 | 5.12 | 3.77 | 4.44 | 4.44 |
| DELTA (mm) | 4.28 | 5.19 | 4.28 | 5.19 | 4.74 | 4.74 |
| CH (%) | 46 | 58 | 46 | 58 | 52 | 52 |
| CLAT (s) | 0.20 | 0.24 | 0.20 | 0.24 | 0.22 | 0.22 |
| CV (mm/s) | 1.11 | 1.25 | 1.11 | 1.25 | 1.18 | 1.18 |
| MCV (mm/s) | 4.20 | 4.25 | 4.20 | 4.25 | 4.22 | 4.22 |
| DV (mm/s) | 1.09 | 1.04 | 1.09 | 1.04 | 1.06 | 1.06 |

Experiment 2

Apraclonidine 0.5% was administered in the right eye of the test subject three (3) times a day for 4 days. After this, dilation using phenylephrine hydrochloride 10% was conducted to investigate the effects of the compound on pupil dilation. See FIGS. 7A-7B and Tables 7-8.

TABLE 7

Figure 7A:
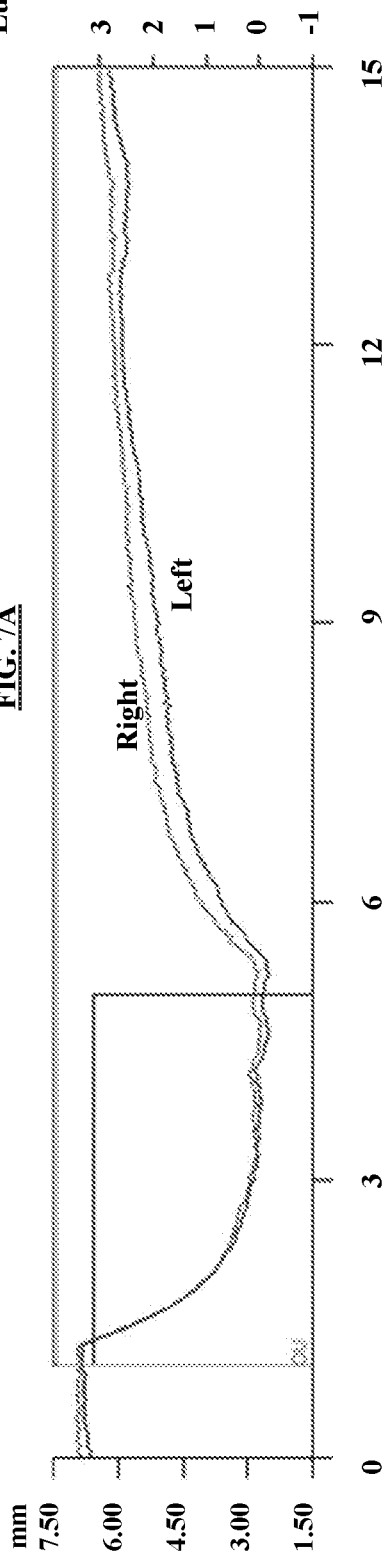
FIGS. 7A-7B are graphs showing pupil dilation wherein the right eye of the subject was administered apraclonidine 0.5% three (3) times a day for 4 days and then administered phenylephrine hydrochloride 10%.

Data derived from FIG. 7A

|  | Right | Left | RPupil Ave | LPupil Ave | RStim Ave | LStim Ave |
|---|---|---|---|---|---|---|
| Max (mm) | 6.91 | 6.82 | 6.91 | 6.82 | 6.87 | 6.87 |
| Min (mm) | 2.71 | 2.54 | 2.71 | 2.54 | 2.62 | 2.62 |
| DELTA (mm) | 4.20 | 4.28 | 4.20 | 4.28 | 4.25 | 4.25 |
| CH (%) | 61 | 63 | 61 | 63 | 62 | 62 |
| CLAT (s) | 0.21 | 0.21 | 0.21 | 0.21 | 0.21 | 0.21 |
| CV (mm/s) | 1.20 | 1.03 | 1.20 | 1.03 | 1.11 | 1.11 |
| MCV (mm/s) | 6.01 | 5.85 | 6.01 | 5.85 | 5.93 | 5.93 |
| DV (mm/s) | 1.19 | 0.97 | 1.19 | 0.97 | 1.08 | 1.08 |

TABLE 8

Figure 7B:
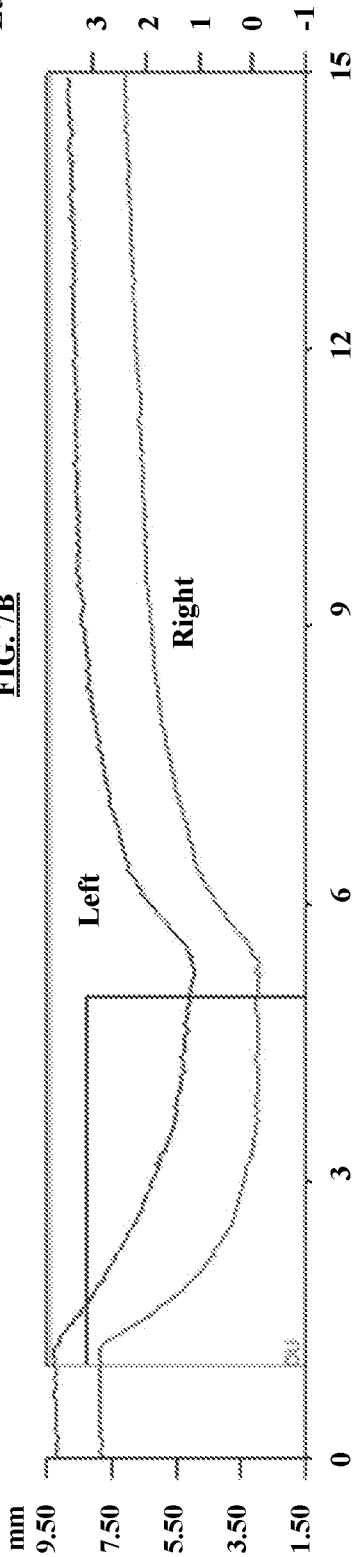

Data derived from FIG. 7B

|  | Right | Left | RPupil Ave | LPupil Ave | RStim Ave | LStim Ave |
|---|---|---|---|---|---|---|
| Max (mm) | 7.83 | 9.25 | 7.83 | 9.25 | 8.54 | 8.54 |
| Min (mm) | 2.95 | 4.95 | 2.95 | 4.95 | 3.95 | 3.95 |
| DELTA (mm) | 4.88 | 4.30 | 4.88 | 4.30 | 4.59 | 4.59 |
| CH (%) | 62 | 46 | 62 | 46 | 54 | 54 |
| CLAT (s) | 0.21 | 0.23 | 0.21 | 0.23 | 0.22 | 0.22 |
| CV (mm/s) | 1.17 | 1.01 | 1.17 | 1.01 | 1.09 | 1.09 |
| MCV (mm/s) | 5.03 | 2.58 | 5.03 | 2.58 | 3.80 | 3.80 |
| DV (mm/s) | 1.18 | 1.24 | 1.18 | 1.24 | 1.21 | 1.21 |

Experiment 3

Dexmedetomidine 0.1% was administered in the right eye of the test subject three (3) times a day for 4 days. After this, dilation using phenylephrine hydrochloride 10% was conducted to investigate the effects of the compound on pupil dilation. See FIGS. 8A-8C and Tables 9-11.

TABLE 9

Figure 8A:
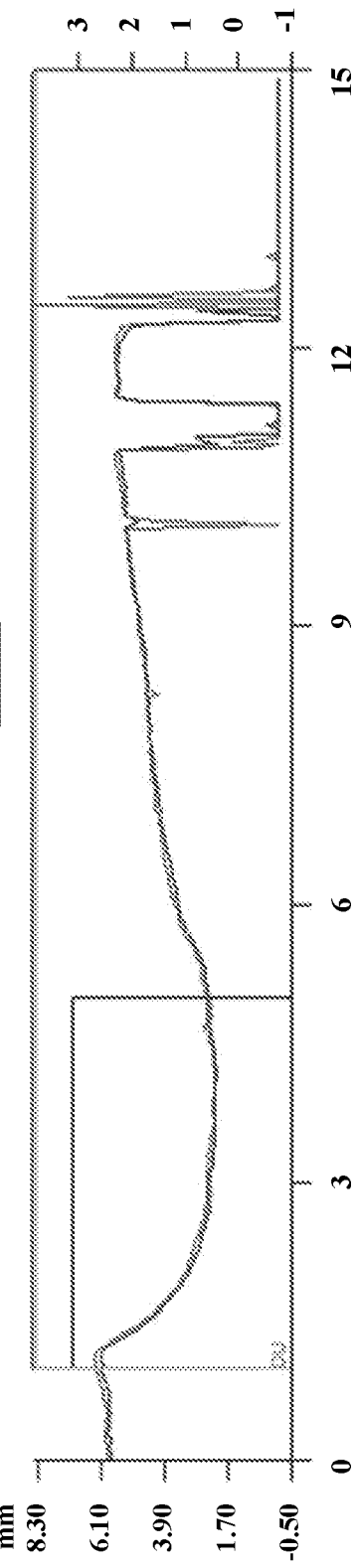
FIGS. 8A-8C are graphs showing pupil dilation wherein the right eye of the subject was administered Dexmedetomidine 0.1% three (3) times a day for 4 days and then administered phenylephrine hydrochloride 10%.

Data derived from FIG. 8A

|  | Right | Left | RPupil Ave | LPupil Ave | RStim Ave | LStim Ave |
|---|---|---|---|---|---|---|
| Max (mm) | 9.40 | 8.96 | 9.40 | 8.96 | 9.18 | 9.18 |
| Min (mm) | 5.12 | 3.77 | 5.12 | 3.77 | 4.44 | 4.44 |
| DELTA (mm) | 4.28 | 5.19 | 4.28 | 5.19 | 4.74 | 4.74 |
| CH (%) | 46 | 58 | 46 | 58 | 52 | 52 |
| CLAT (s) | 0.20 | 0.24 | 0.20 | 0.24 | 0.22 | 0.22 |
| CV (mm/s) | 1.11 | 1.25 | 1.11 | 1.25 | 1.18 | 1.18 |
| MCV (mm/s) | 4.20 | 4.25 | 4.20 | 4.25 | 4.22 | 4.22 |
| DV (mm/s) | 1.09 | 1.04 | 1.09 | 1.04 | 1.06 | 1.06 |

TABLE 10

Figure 8B:
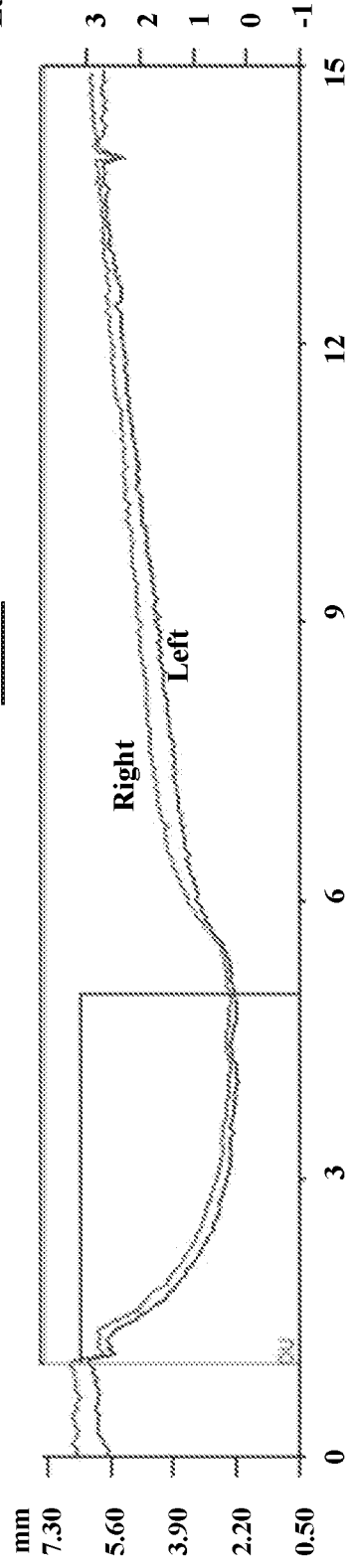

Data derived from FIG. 8B

|  | Right | Left | RPupil Ave | LPupil Ave | RStim Ave | LStim Ave |
|---|---|---|---|---|---|---|
| Max (mm) | 6.57 | 6.03 | 6.57 | 6.03 | 6.30 | 6.30 |
| Min (mm) | 2.38 | 2.20 | 2.38 | 2.20 | 2.29 | 2.29 |
| DELTA (mm) | 4.19 | 3.83 | 4.19 | 3.83 | 4.01 | 4.01 |
| CH (%) | 64 | 64 | 64 | 64 | 64 | 64 |
| CLAT (s) | 0.38 | 0.34 | 0.38 | 0.34 | 0.36 | 0.36 |
| CV (mm/s) | 1.06 | 1.27 | 1.06 | 1.27 | 1.16 | 1.16 |
| MCV (mm/s) | 5.84 | 4.99 | 5.84 | 4.99 | 5.42 | 5.42 |
| DV (mm/s) | 0.96 | 0.94 | 0.96 | 0.94 | 0.95 | 0.95 |

TABLE 11

Figure 8C:
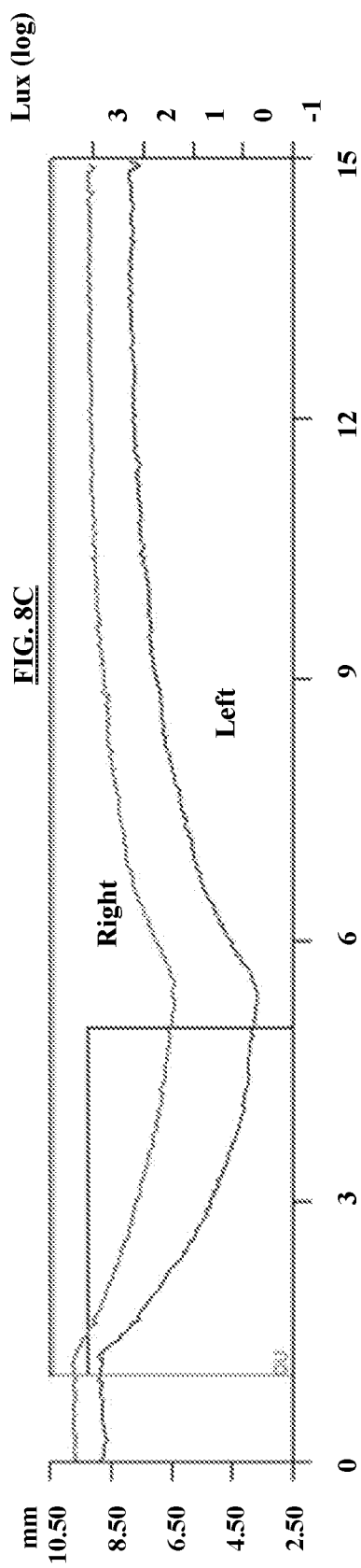

Data derived from FIG. 8C

|  | Right | Left | RPupil Ave | LPupil Ave | RStim Ave | LStim Ave |
|---|---|---|---|---|---|---|
| Max (mm) | 9.73 | 8.81 | 9.73 | 8.81 | 9.27 | 9.27 |
| Min (mm) | 6.42 | 3.68 | 6.42 | 3.68 | 5.05 | 5.05 |
| DELTA (mm) | 3.31 | 5.13 | 3.31 | 5.13 | 4.22 | 4.22 |
| CH (%) | 34 | 58 | 34 | 58 | 46 | 46 |
| CLAT (s) | 0.16 | 0.24 | 0.16 | 0.24 | 0.20 | 0.20 |
| CV (mm/s) | 0.76 | 1.22 | 0.76 | 1.22 | 0.99 | 0.99 |
| MCV (mm/s) | 2.49 | 4.00 | 2.49 | 4.00 | 3.24 | 3.24 |
| DV (mm/s) | 0.80 | 1.08 | 0.80 | 1.08 | 0.94 | 0.94 |

A washout period of multiple months was undertaken in between each experiment. Repeat dilation of both eyes was conducted after this washout period to ensure both pupils were relatively similar to the control dilation and no effects of the compound remained.

Pupil measurements were obtained using a Neuroptics pupillometer. Parameters were as follows: Scotopic conditions for 1 second, followed by photopic conditions for 4 seconds (1258.925 lux), followed by scotopic conditions for 10 seconds. This allowed for investigation of scotopic pupil size, photopic pupil size, and scotopic pupil size recovery after the light stimulus concluded.

Example 1: The Effect of Brimonidine on Pupil Dilation

A human subject was administered an ophthalmic formulation of brimonidine 0.15% solution (1 drop, 3 times per day) for 4 days in his right eye. The pupils of the subject's pretreated right eye and untreated control left eye were then measured under both scotopic and photopic conditions for baseline measurements (FIG. 6A). Photopic conditions consisted of a 4 second window where a light was shining in both eyes simultaneously. Under both scotopic and photopic conditions, the pretreated eye remained less dilated and also dilated much more slowly upon return to scotopic conditions.

After baseline testing, the subject was then administered a second ophthalmic formulation containing 2.5% phenylephrine to both eyes. 30 minutes after instillation of 2.5% phenylephrine, the pupils of the subject were then measured again under both scotopic and photopic conditions (FIG. 6B). Under scotopic conditions, both the pretreated and control eyes remained equally dilated. Under photopic conditions, the pretreated eye remained more dilated than the control eye, reversing the trend observed during baseline testing prior to administration of phenylephrine. Return to scotopic conditions showed that the pretreated eye dilated more rapidly than the control eye. These results suggest that the brimonidine pretreatment sensitized the subject's pretreated eye to the phenylephrine when compared to the untreated eye.

The experiment was repeated at a higher dosage wherein the subject was administered a second ophthalmic formulation containing 10% phenylephrine to both eyes. 30 minutes after instillation of 10% phenylephrine, the pupils of the subject were then measured under both scotopic and photopic conditions (FIG. 6C). Under scotopic conditions, the pretreated eye was more dilated than the control eye. Under photopic conditions, the pretreated eye remained much more dilated than the control eye, reinforcing the observation in the 2.5% phenylephrine experiment. Upon removal of the light, the pretreated eye dilated more rapidly than the control eye. Overall, there was an average 36% increase in dilation size observed in the pretreated eye compared to the control eye. Because the area of a circle is dependent on the radius squared (area of a circle=$\pi r^2$), the increase in area that is created from a increasing the pupil dilation size is not linear. This advantage is exemplified in this experiment in FIG. 6C, where, under photopic conditions, the control eye had a pupil area of 11.16 mm$^2$ and the pre-treated eye has a pupil area of 20.59 mm$^2$. This translated into an increase in surgical workspace by ~85%.

Example 2: Pupil Dilation Comparative Studies

Additional experiments were conducted as described in Example 1 using apraclonidine 0.5% or dexmedetomidine 0.1% in place of the brimonidine pretreatment. The results were then compared.

Table 12 shows pupil size after dilation with phenylephrine hydrochloride 10% in the treated eye group and non-treated eye group. Table 13 shows surgical work area after dilation with phenylephrine hydrochloride 10% in the treated eye group and non-treated eye group. As α2:α1 affinity increased (see Table 1), the efficacy of the medication to improve pupillary dilation increased. Tables 14 and 15 highlight these findings. Specifically, brimonidine tartrate 0.15% was able to increase surgical work area by approximately 103% compared to the pre-treatment control dilation amount in the same eye. Dexmedetomidine was able to increase surgical work area by an even larger amount, +220%, compared to the pre-treatment control dilation amount in the same eye. In contrast, treatment with apraclonidine hindered dilation in this experiment rather than enhancing it. Without intending to be limited to any particular theory, this is likely because of its lower α2/α1 affinity ratio, allowing it to interact with the α1 receptors more readily than brimonidine or dexmedetomidine, leading to a de-sensitization of the iris to other α1 agonists, in this case, phenylephrine.

TABLE 12

Pupil size (mm) under photopic conditions (1258.925 lux) after dilation with phenylephrine 10%

| Pre-treatment | Treated eye | Non-treated eye |
| --- | --- | --- |
| none | 3.59 | 3.36 |
| apraclonidine | 2.95 | 4.95 |
| brimonidine | 5.12 | 3.77 |
| dexmedetomidine | 6.42 | 3.68 |

TABLE 13

Surgical Work area (mm$^2$) under photopic conditions (1258.925 lux) after dilation with phenylephrine 10%

| Pre-treatment | Treated eye | Non-treated eye |
| --- | --- | --- |
| none | 10.1171585 | 8.862336 |
| apraclonidine | 6.8314625 | 19.2344625 |
| brimonidine | 20.578304 | 11.1571265 |
| dexmedetomidine | 32.354874 | 10.630784 |

TABLE 14

Effect of pretreatment: dilation pre and post treatment with α 2 agonist (treated eye vs control measurements of same eye)

| | Pupil size change (%) | Surgical work area change (%) |
| --- | --- | --- |
| Apraclonidine | −17.82729805 | −32.47647054 |
| Brimonidine | +42.6183844 | +103.4000357 |
| Dexmedetomidine | +78.83008357 | +219.8019879 |

TABLE 15

Effect of pretreatment: non-treated eye dilation compared to treated eye dilation

| | Pupil size change (%) | Surgical work area (%) |
| --- | --- | --- |
| Apraclonidine | −40.4040404 | −64.483216 |
| Brimonidine | +35.80901857 | +84.44089524 |
| Dexmedetomidine | +74.45652174 | +204.3507798 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for enhancing dilation of a pupil of a subject, the method comprising administering to the subject,
   a first composition comprising at least one alpha-2 selective agonist, or a salt or solvate thereof; and
   a second composition comprising at least one alpha-1 agonist or a salt or solvate thereof, wherein administering comprises administering at least one dose of the first composition to a subject's eye and subsequently administering at least one hour up to 30 days later at least one dose of the second composition to the subject's eye, wherein the second composition induces pupil dilation, and the second composition comprises at least one alpha-1 agonist selected from the group consisting of cirazoline, epinephrine, etilefrine, metaraminol, methoxamine, midodrine, naphazoline, norepinephrine, oxymetazoline, phenylephrine, pseudoephedrine, tetrahydrozoline, and synephrine, or a salt or solvate thereof, and wherein the first composition has an alpha-2:alpha-1 affinity ratio of greater than 200.

2. The method of claim 1, wherein the first composition comprises at least one alpha-2 selective agonist-selected from the group consisting of: amitraz, cannabigerol, brimonidine, detomidine, dexmedetomidine, fadolmidine, guanabenz, guanfacine, lofexidine, marsanidine, 7-Me-marsanidine, medetomidine, methamphetamine, mivazerol, 4-NEMD, rilmenidine, romifidine, talipexole, tiamenidine, tizanidine, tolonidine, vortioxetine, and xylazine, or a salt or solvate thereof.

3. The method of claim 1, wherein the second composition comprises at least one of epinephrine and phenylephrine, or a salt or solvate thereof.

4. The method of claim 1, wherein the first composition comprises at least one of brimonidine and dexmedetomidine, and wherein the second composition comprises at least one of phenylephrine and epinephrine.

5. The method of claim 1, wherein the first composition comprises a concentration from about 0.001% to about 50% (v/v) per dose; and wherein the second composition comprises a concentration from about 0.001% to about 50% (v/v) per dose.

6. The method of claim 1, wherein the second composition is administered to the subject from about 1 day to about 10 days after administration of the first composition.

7. The method of claim 1, wherein the first composition is administered to the subject two or more times before the second composition is administered.

8. The method of claim 1, wherein the first composition is administered at least once per day for about 1 day to about 10 days.

9. The method of claim 1, wherein the first composition is a pharmaceutical composition formulated for topical administration.

10. The method of claim 1, wherein the first composition is a pharmaceutical composition formulated as an ophthalmic drop, ophthalmic ointment, ophthalmic gel, ophthalmic spray or ophthalmic lotion.

11. The method of claim 1, wherein the second composition is a pharmaceutical composition formulated for topical administration.

12. The method of claim 1, wherein the second composition is a pharmaceutical composition formulated as an ophthalmic drop, ophthalmic ointment, ophthalmic gel, ophthalmic spray, ophthalmic lotion, or ophthalmic intracameral injection.

13. The method of claim 1, wherein the first composition and the second composition are administered to the subject by at least one of the following routes: topically; through intracameral injection; or, directly applied to at least one portion of the eye of the subject.

14. A kit comprising at least one dose of a first composition comprising at least one alpha-2 selective agonist; and at least one dose of a second composition comprising at least one alpha-1 agonist wherein and the second composition comprises at least one alpha-1 agonist selected from the group consisting of cirazoline, epinephrine, etilefrine, metaraminol, methoxamine, midodrine, naphazoline, norepinephrine, oxymetazoline, phenylephrine, pseudoephedrine, tetrahydrozoline, and synephrine, or a salt or solvate thereof, and wherein the first composition has an alpha-2:alpha-1 affinity ratio of greater than 200; and at least one container.

15. The kit of claim 14, wherein the first composition comprises at least one alpha-2 selective agonist-selected from the group consisting of, amitraz, cannabigerol, brimonidine, detomidine, dexmedetomidine, fadolmidine, guanabenz, guanfacine, lofexidine, marsanidine, 7-Me-marsanidine, medetomidine, methamphetamine, mivazerol, 4-NEMD, rilmenidine, romifidine, talipexole, tiamenidine, tizanidine, tolonidine, vortioxetine, and xylazine, or a salt or solvate thereof.

16. The kit of claim 14, wherein the kit comprises at least two doses of the first composition and at least one dose of the second composition.

17. The kit of claim 14, further comprising materials containing instructions for using the at least one dose of a first composition comprising at least one alpha-2 selective agonist and the at least one dose of a second composition comprising at least one alpha-1 agonist.

18. The kit of claim 14, wherein the at least one alpha-2 selective agonist comprises at least one of brimonidine and dexmedetomidine, and
wherein the at least one alpha-1 agonist comprises at least one of phenylephrine and epinephrine.

19. The method of claim 13, wherein applying directly to at least one portion of the eye of the subject comprises applying directly to at least one of the cornea, iris, sclera, conjunctiva, or anterior chamber of the subject's eye.

20. The method of claim 1, wherein the first composition has an affinity ratio of alpha-2:alpha-1 of about 800 or greater.

21. The method of claim 1, wherein the first composition has an affinity ratio of alpha-2:alpha-1 of about 976 or greater.

22. The method of claim 1, wherein administering the at least one dose of the first composition to the subject's eye comprises administering the at least one dose of the first composition to the subject's eye to induce at least one of an increase in the amount or sensitivity of alpha 1 receptors on iris dilator muscles of the subject's eye.

23. The method of claim 1, wherein the first composition comprises dexmedetomidine.

24. The method of claim 1, wherein the first composition comprises a concentration of about 0.01% to about 0.5% (v/v) per dose.

25. The method of claim 1, wherein the first composition comprises an ophthalmic drop.

26. The method of claim 1, further comprising administering to the subject the first composition as an ophthalmic drop twice to four times per day for 1 day up to 10 days at a dose concentration of about 0.01% to about 0.5% (v/v) dexmedetomidine; and administering the second composition about 1 day up to about 10 days after administering the first composition.

* * * * *